United States Patent [19]
Shine et al.

[11] Patent Number: 6,093,151
[45] Date of Patent: Jul. 25, 2000

[54] MATERNAL AND FETAL MONITOR

[75] Inventors: David J. Shine, Hamden; Judith A. Adamowich, Bristol, both of Conn.

[73] Assignee: GE Marquette Medical Systems, Inc., Milwaukee, Wis.

[21] Appl. No.: 09/179,723

[22] Filed: Oct. 14, 1998

[51] Int. Cl.[7] ........................................................ A61B 5/00
[52] U.S. Cl. .................... 600/485; 128/897; D24/231; 600/551; 600/591
[58] Field of Search ..................................... 600/491–486, 600/551, 500, 300, 591, 479; 128/897–898, 900, 920–925

Primary Examiner—Cary O'Connor
Assistant Examiner—Michael Astorino
Attorney, Agent, or Firm—Michael Best & Friedrich; Christian G. Cabou; Phyllis Y. Price

[57] ABSTRACT

A maternal blood pressure measuring method including the steps of periodically initiating a maternal blood pressure measurement, sensing uterine activity, preventing the initiation or continuation of a blood pressure measurement during uterine contraction, initiating a blood pressure measurement upon the cessation of uterine contractions and a processor programmed to perform these functions.

17 Claims, 6 Drawing Sheets

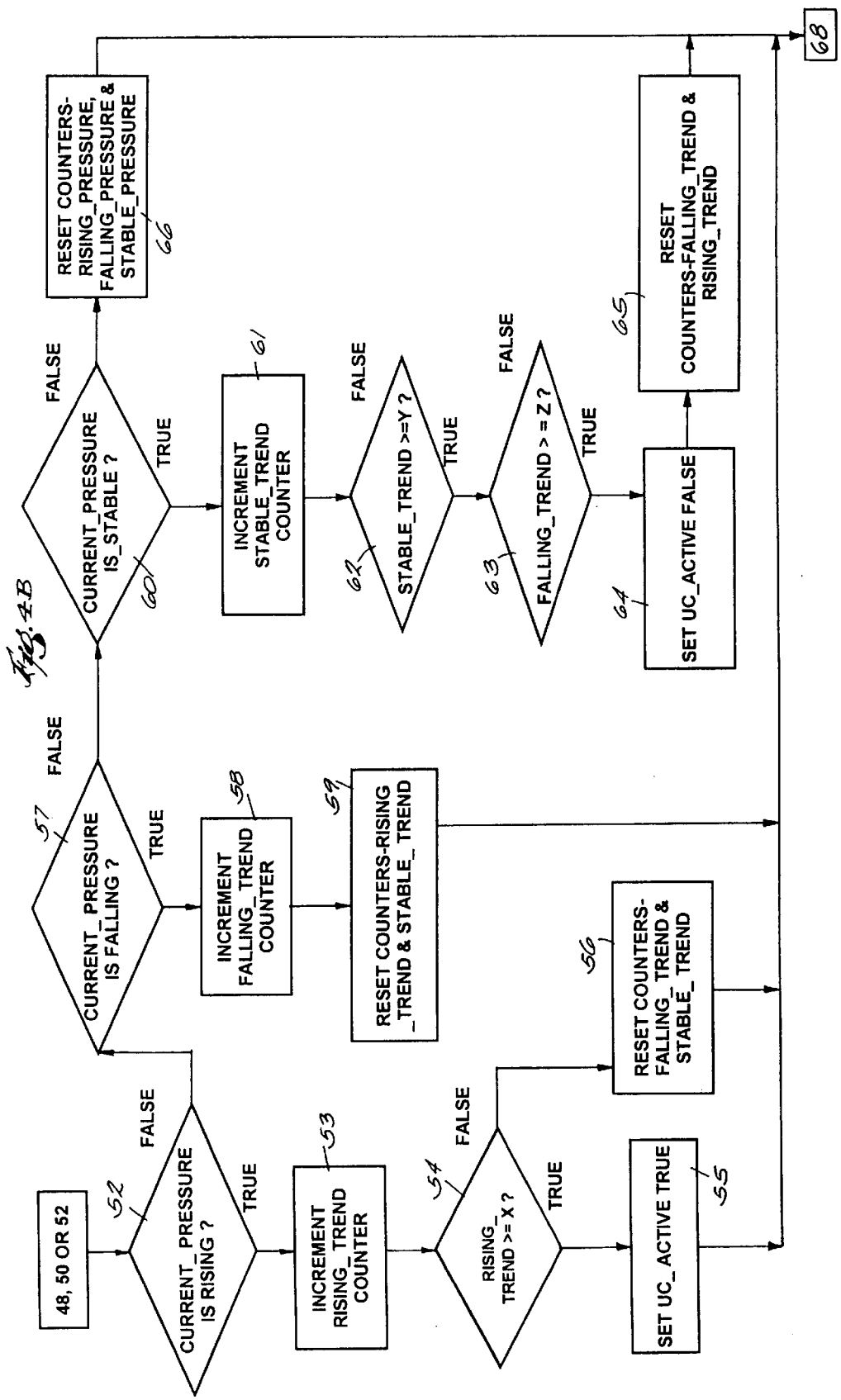

MATERNAL AND FETAL MONITOR

BACKGROUND OF THE INVENTION

This invention relates to maternal and fetal monitors and more particularly a system wherein the measurement of maternal blood pressure is controlled during uterine contractions.

Maternal/fetal monitors are employed for monitoring both maternal and fetal vital signs prior to, during and after delivery. These vital signs typically include fetal heart rate measured by ultrasound, maternal and fetal ECG's and pulse oximetry; maternal blood pressure and uterine activity. Maternal blood pressure is typically monitored using a conventional pressure measuring system. Such blood pressure measurements may be initiated manually or automatically on a periodic basis. However, when a maternal blood pressure measurement is made during a uterine contraction, the results are often diagnostically inaccurate and the patient may experience additional discomfort.

SUMMARY OF THE INVENTION

An object of the invention is to provide a new and improved maternal and fetal monitoring method and apparatus.

Another object of the invention is to provide a new and improved maternal blood pressure monitoring method and apparatus.

A further object of the invention is to provide a system and apparatus for controlling the initiation of maternal blood pressure measurements in relation to uterine contractions.

Still another object of the invention is to provide a method and apparatus in which the initiation of maternal blood pressure measurements is prevented during uterine contractions.

It is a further object of the invention to provide a method and apparatus for delaying the initiation of a maternal blood pressure measurement during uterine contractions.

Yet another object of the invention is to provide a system and apparatus which terminate a maternal blood pressure measurement in progress upon the occurrence of a uterine contraction.

It is a still further object of the invention to provide a method and apparatus for detecting the onset of uterine contractions.

In general terms, the invention comprises a maternal monitoring method including the steps of periodically initiating a maternal blood pressure measurement, sensing uterine activity, preventing the initiation or continuation of the blood pressure measurement during uterine contractions and initiating a blood pressure measurement after the cessation of the uterine contraction.

According to another aspect, the invention comprises means for measuring maternal blood pressure, means for periodically initiating the operation of the maternal blood pressure measuring means, means for sensing uterine contractions, means for preventing the initiation or continuation of a blood pressure measurement during uterine contractions, and means for initiating a blood pressure measurement after the cessation of uterine contractions.

According to another aspect, the invention comprises the method of acquiring uterine contraction data, determining whether uterine pressure is increasing, decreasing or stable to identify a uterine contraction to determine the trend of the uterine activity data, and determining the onset of uterine activity from the comparison.

BRIEF DESCRIPTION OF THE DRAWINGS

FIGS. 4A, 4B and 4C are flow charts illustrating the method according to the invention.

DETAILED DESCRIPTION OF THE PREFERRED EMBODIMENT

Figure 1:
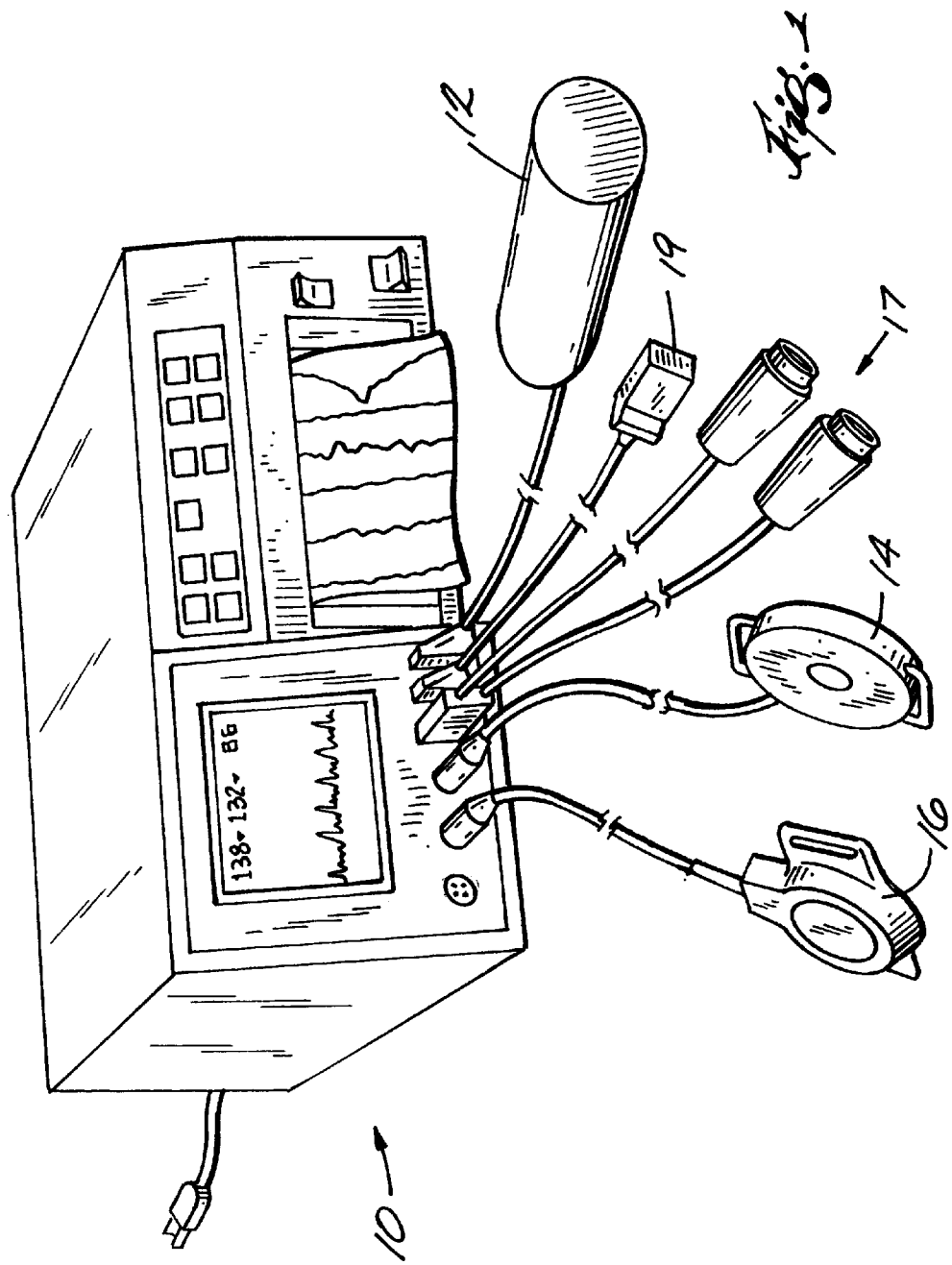
FIG. 1 illustrates a maternal/fetal monitor in which the method according to the invention may be performed.

FIG. 1 shows a maternal/fetal monitor 10 in which the method according to the invention may be performed. Monitor 10 may be suitably connected to a plurality of sensors, transducers and electrodes for sensing various maternal and/or fetal physiological conditions. These may include, for example, a non-invasive blood pressure measuring device 12 for maternal blood pressure measurement and a uterine contraction sensor 14. While the noninvasive blood pressure measuring device 12 is show to comprise a pressure cuff, those skilled in the art will appreciate that any type of noninvasive blood pressure measuring system may be employed. When a pressure cuff is used, it is inflated either manually or automatically at preselected intervals to a pressure above the patient's systolic pressure and then deflated to a pressure below the patient's diastolic pressure. By sensing the commencement of intermittent and continuous blood flow as the pressure is reduced, the patient's systolic and diastolic blood pressure can be determined in a manner well known in the art.

Uterine activity may be sensed in any well known manner, such as by means of a tocodynamometer 14 which is positioned on the maternal abdomen, and may include, for example, a strain gauge which senses changes in uterine pressure. An alternate uterine activity sensor may comprise a pressure sensor (not shown) which is positioned by a catheter in the fluid in the maternal uterus. It will be appreciated that these are intended as examples only and other types of uterine activity sensors may also be employed.

The maternal/fetal monitor 10 may also include other sensors such as an ultrasonic sensor 16 for externally sensing the fetal heart rate; cables 17 for fetal ECG measurement, and sensors 19 for measuring fetal and maternal pulse oximetry. These sensors are all conventional and need not be discussed in detail for purposes of understanding the present invention.

Figure 2:
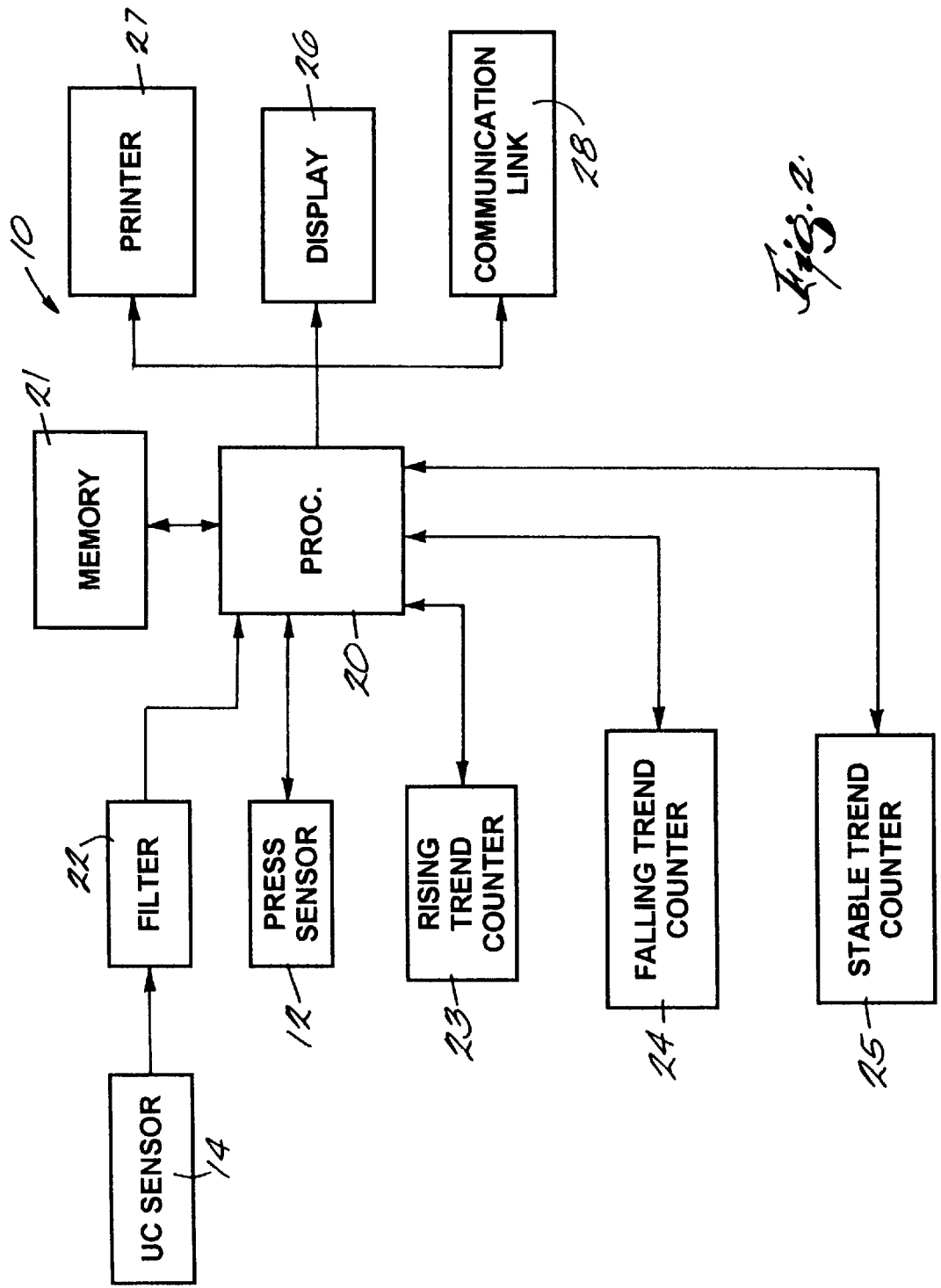
FIG. 2 is a block diagram illustrating a portion of the apparatus of FIG. 1.

FIG. 2 is a block diagram illustrating the apparatus 10 in which the method according to the invention is performed. The apparatus includes a processor 20 having a memory 21. The processor 20 receives uterine contraction data acquired from sensor 14 and filtered at 22. This data is averaged on a periodic basis and compared by processor 20 with uterine contraction data stored in memory 21 to determine whether the trend is rising, falling or stable. This information is utilized to increment the appropriate one of the trend counters 23, 24 or 25. The trend counters record trends in the uterine activity data over multiple periods. Based on the counter values, the processor makes an assessment of the trend in the uterine activity shape, that is, rising, falling or stable. If the trend is rising or falling, the processor terminates any blood pressure measurement in progress or delays any measurement scheduled. After a time delay, a blood pressure measurement is initiated and the measurement is output to a display 26, a printer 27 and/or a communication link 28. The length of the time delay is dependent upon the period of the uterine contraction. The delay period for resuming a blood pressure measurement is a function of the uterine activity trend. The trend counters 23, 24 and 25 are used by the algorithm to identify trend shapes. A counter value or combination of values, is used to determine that a uterine contraction has begun or ended, which may dictate the halting or resumption of a blood pressure measurement. If it is determined that the uterine contraction has ended the blood pressure measurement is started or resumed.

Figure 3:
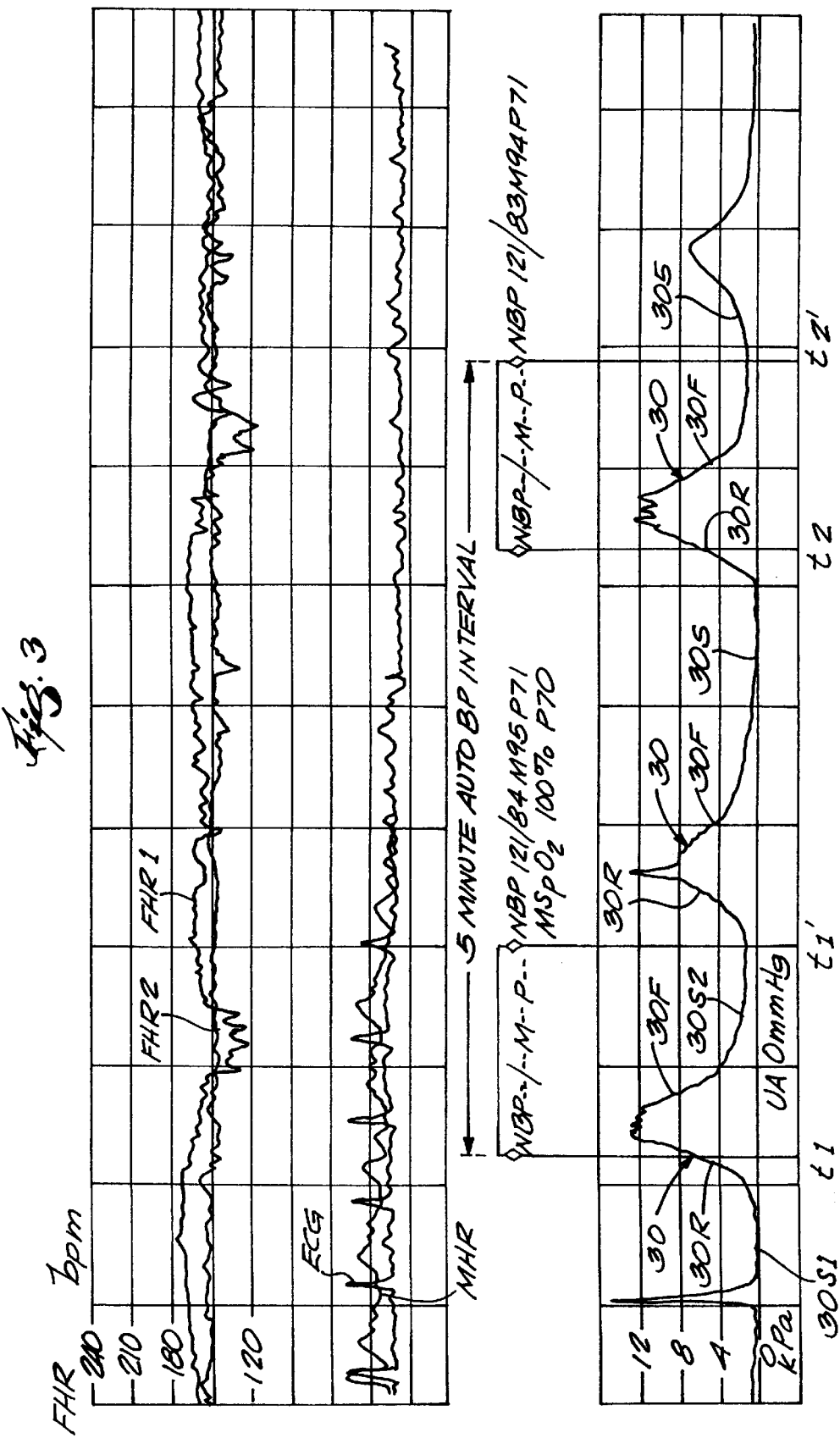
FIG. 3 is a strip chart illustrating the operation of the method in accordance with the invention.

The uterine activity trace from printer 27 is identified by the reference numeral 30 in FIG. 3. The trends of the uterine activity wave form are characterized as rising 30R; falling 30F and stable 30S. All characterizations in the trend are made, based on changes or deltas in the pressure or relative measurement units. A trend which establishes a stable pattern, that is, not rising or falling, may be thought of as representing a base line 30S. Identifying a uterine contraction involves recognizing a trend which has risen from an established base line 30S1, and then falls back toward the base line and restabilizes at 30S2, but not necessarily at the original base line.

The processor is also programmed to initiate maternal blood pressure measurements at periodic intervals which, in the illustrated example, is five minutes. These times are identified as t1 and t2 in FIG. 3. It can be seen that times t1 and t2 occur during a uterine contraction 30. The computer is programmed so that once a uterine contraction trend has been analyzed and the onset of a uterine contraction identified, an active blood pressure reading occurring during a uterine contraction 30 is terminated and restarted following the termination of the uterine contraction, or an automatic blood pressure reading which is scheduled to occur during the uterine contraction is delayed until after the uterine contraction has been completed. With reference to FIG. 3, the blood pressure measurements are delayed from time t1 to time t1' and from time t2 until time t2'. This is symbolized on the strip chart of FIG. 3 by the notation at time t1 NBP-/-M-P- and by the notation NBP121/84 M 95 P 71 at time t1', to indicate that no reading was taken at time t1, and to indicate the rescheduled blood pressure measurement has been completed, at time t1. Similar notations are shown at times t2 and t2'.

Also illustrated in FIG. 3 are heart rate trends FHR1 and FHR2, which indicate fetal heart rates measured by the ultrasonic devices or fetal scalp electrodes. The strip chart may also include other wave forms, such as, for example, the maternal heart rate MHR and the maternal and fetal electrocardiogram ECG.

Provision may also be provided within the program operating processor 20 to prevent the indefinite postponement of a blood pressure measurement. This is necessary to insure that a blood pressure reading is taken even in the presence of very frequent uterine contractions.

Figure 4A:
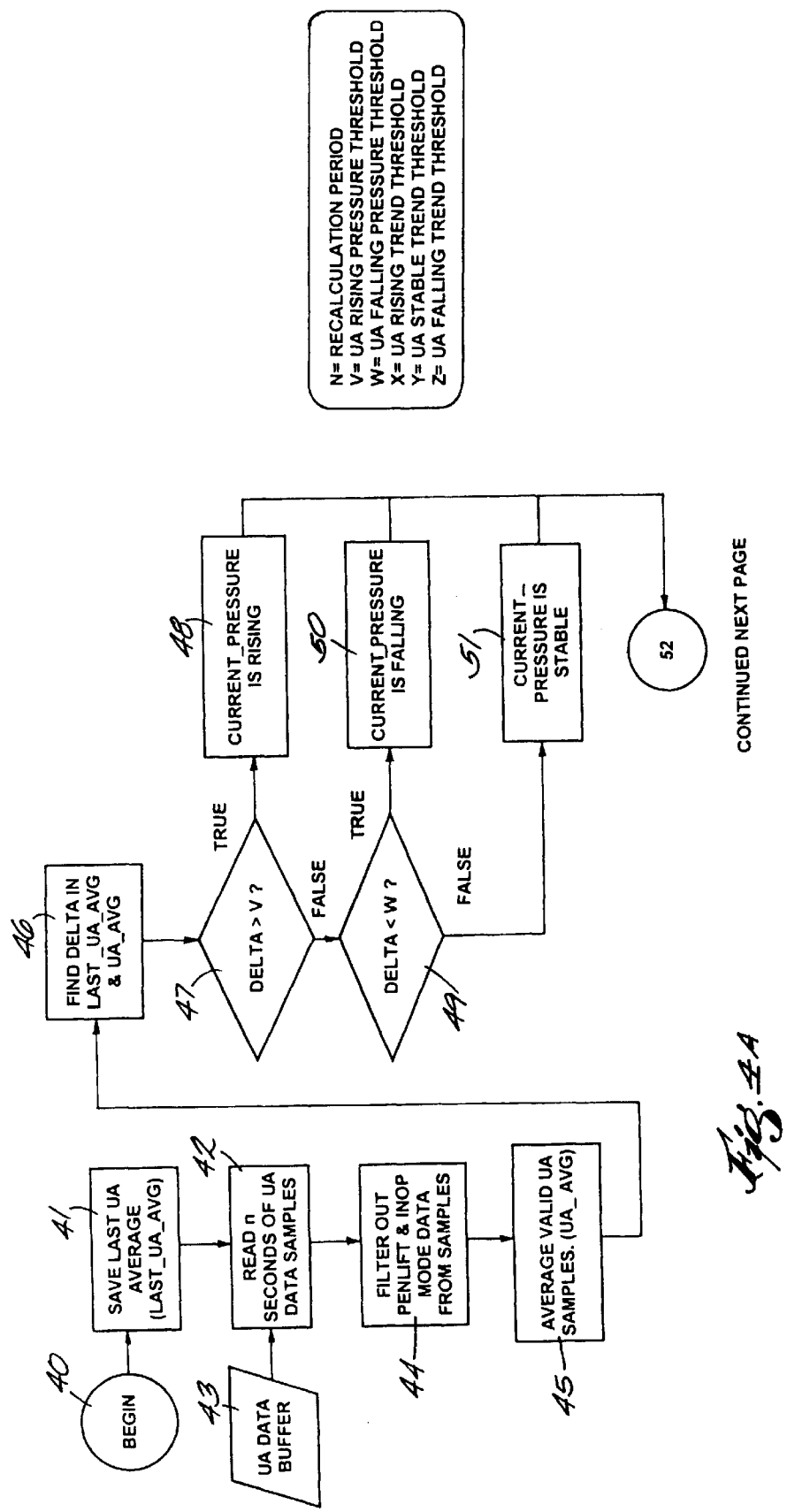
Figure 4C:
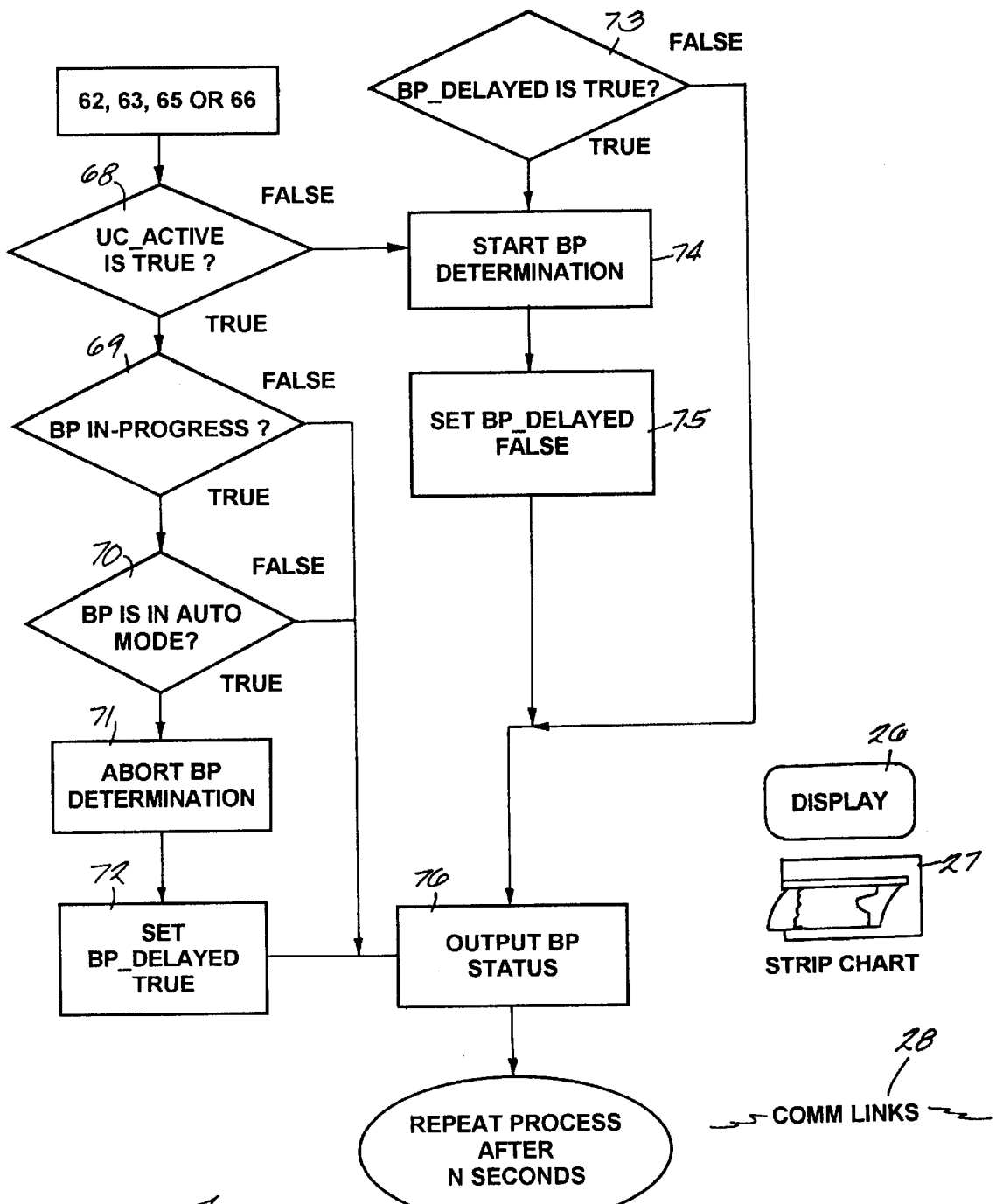

The processor 20 is programmed to perform the process according to the preferred embodiment as illustrated in FIGS. 4A, 4B and 4C. The program is initiated at step 40. The uterine activity average from the previous cycle of step 42, is stored in memory at 41. In addition, n seconds of uterine activity data samples are read at step 42. This uterine activity data is provided through a buffer 43. Penlift and inoperative mode data from the samples are filtered at step 44. At step 45, the filtered valid uterine activity samples are averaged.

In steps 46–51, the program determines the mode of the uterine activity samples, that is, whether they are rising, falling, or stable. Specifically, at step 46, the delta between the current uterine activity average and the uterine activity average from the last period is determined. If the delta is greater than v (positive trend) at step 47, the uterine activity is rising as indicated at step 48. If the delta is less than w (negative trend), the uterine activity is falling as indicated at step 50. However, if the uterine activity is neither rising or falling, this indicates that the uterine activity is stable as indicated at step 51.

The uterine activity pressure thresholds combined with the averaging period are important parameters in identifying rising or falling slopes in the uterine activity wave form, as opposed to slopes indicative of a changing base line, artifact or fetal movement. Gradual changes in uterine activity data are more characteristic of a change in uterine activity base line and rapid changes in uterine activity data are more characteristic of artifacts. The determinations at steps 47 and 49 comprises a prefiltering required before the trend shape identification process can proceed.

The program next determines the shape of the uterine activity at steps 52, 57 and 60 and sets the trend counters 23, 24 and 25 which record trends of uterine activity data over multiple periods. An assessment of trend shape is determined from the counter values. Specifically, if the program determines that the current pressure is rising at step 52, the program increments the rising trend counter 23 at step 53. The program then determines at step 54 whether the rising trend is greater than the uterine activity rising trend x. If true, the program sets the uterine contraction active as true at step 55. If not true, the program resets the falling trend counter 24 and the stable trend counter 25 to zero at step 56.

If at step 52, the current pressure is not rising, the program determines at step 57 if the current pressure is falling. If true, the program increments the falling trend counter 24 at step 58 and resets the rising trend counter 23 and the stable trend counter 25 to zero at step 59.

If the program determines at step 57 that the current pressure is not falling, the program determines at step 60 whether the current pressure is stable. If true, the program increments the stable trend counter 25 at step 61. At step 62, the program determines whether the stable trend is greater than the uterine activity stable trend y. If true, the program proceeds to step 63 where the program determines if the falling trend is greater than the uterine activity falling trend threshold x. If true, the program sets the uterine contraction active as false at step 64 and the rising trend counter 23 and the falling trend counter 24 are reset to zero at step 65.

If at step 60 the program determines that the current pressure is not stable, the program resets the rising trend counter 23, the falling trend counter 24 and the stable trend counter 25 to zero at step 66. After steps 55, 56, 59 or 66, or if the program determines at step 62 that the stable trend is not greater than the uterine activity stable trend threshold y at step 62 or if the program determines at step 63 that the falling trend is not greater than the uterine activity falling trend threshold z et al., the program proceeds to step 68.

The next portion of the program commencing with step 68 in FIG. 4C, inhibits or initiates a blood pressure measurement depending on the uterine activity trend. In particular, at step 68, the program determines whether the uterine contraction activity is true. If true, the program determines at step 69 whether a blood pressure measurement is in progress and if true, the program determines whether the blood pressure is in an automatic mode at step 70. If true, the blood pressure determination is aborted at step 71 and at step 72 the program sets the blood pressure delay at true.

If at step 68, the program determines that the uterine contraction is not set at true, the program determines at step 73 whether the blood pressure delay is set at true. If true, a blood pressure determination is initiated at step 74 and the blood pressure delay is set at false at step 75.

If the program determines at step 69 that a blood pressure measurement is not in progress or at step 70 that blood pressure is not in automatic mode or if at step 72 the program sets the blood pressure delay at true or after the program determines at step 73 that the blood pressure delay is not set at true or after the blood pressure delay is set at false at step 75, the program outputs the blood pressure status at step 76 to the display 26, the printer 27 and/or the communication link 28.

Under certain conditions atypical uterine activity patterns may occur. For example, failure to reference uterine activity can produce a pattern with truncated peaks and misplacement of the sensor 14 can produce an inverted trend pattern. Under these circumstances, the counters will expire causing counter reset and/or a new baseline is established. In the case of an inverted uterine activity trend, the program may react to uterine contraction onset as a falling edge and subsequently delay the blood pressure measurement.

It can be seen that the program determines whether an automatic blood pressure measurement is in progress during a uterine contraction in which case, the blood pressure determination is aborted and restarted after the uterine contraction has ceased. Similarly, if a uterine contraction is identified and an automatic blood pressure is scheduled to begin, such as at time t1 in FIG. 3, the determination is delayed until time t1' after the uterine contraction has ceased. Finally, the system counts the number of blood pressure delays without a completed measurement. After a predetermined number of such consecutive delays (usually 1 or 2), the measurement will proceed regardless of the occurrence of a uterine contraction. This prevents the indefinite postponement of blood pressure readings. The strip chart of FIG. 3 indicates that the blood pressure determination has been delayed.

We claim:

1. A maternal monitoring method including the steps of periodically initiating a scheduled maternal blood pressure measurement, sensing the occurrence of uterine contractions, preventing the initiation or continuation of a blood pressure measurement during a uterine contraction, and initiating the blood pressure measurement upon the cessation of the uterine contraction.

2. The method set forth in claim 1 and including the steps of determining whether uterine pressure is increasing, decreasing or stable to identify a uterine contraction, initiating blood pressure measurements periodically, determining if a blood pressure measurement is in progress, terminating any blood pressure measurements in progress if a uterine contraction is occurring and restarting the blood pressure measurement after the uterine contraction is completed.

3. The method set forth in claim 2 and including the step of averaging uterine activity samples for preselected period, determining the difference between successive uterine activity averages determining if the difference is above a positive threshold or below a negative threshold to determine whether the uterine pressure is rising, falling or stable.

4. The method set forth in claim 3 and including the step of recording trends in uterine activity data over multiple periods and assessing the trend to determine whether a uterine contraction is in progress.

5. The method set forth in claim 1 and including the steps of determining whether uterine pressure is rising, falling or stable to indicate whether a uterine contraction is occurring, periodically initiating maternal blood pressure measurements, delaying any blood pressure measurement scheduled during a uterine contraction, and initiating the blood pressure measurement after the uterine contraction is completed.

6. The method set forth in claim 5 and including the step of averaging uterine activity samples for preselected period, determining the difference between successive uterine activity averages, determining if the difference is above a positive threshold or below a negative threshold to determine whether the uterine pressure is rising, falling or stable.

7. The method set forth in claim 6 and including the step of recording trends in said rising, falling or stable uterine pressure measurements over multiple periods and assessing the trend to determine whether a uterine contraction is in progress.

8. The method set forth in claim 1 and including the steps of determining whether uterine pressure is rising, falling or stable to indicate whether a uterine contraction is occurring, periodically initiating maternal blood pressure measurements, delaying any blood pressure measurement scheduled during a uterine contraction, and initiate the blood pressure measurement after uterine contraction is completed.

9. Apparatus for monitoring maternal blood pressure including means for periodically initiating a maternal blood pressure measurement, means for sensing uterine contractions, means for preventing the initiation or continuation of a blood pressure measurement during a uterine contraction, and means for initiating a blood pressure measurement upon the cessation of the uterine contraction.

10. The apparatus set forth in claim 9 and including means for determining whether uterine pressure is increasing, decreasing or stable to identify a uterine contraction, means for periodically initiating maternal blood pressure measurements, means for determining if a blood pressure measurement is in progress, means for terminating any blood pressure measurements in progress if a uterine contraction is occurring, and means for restarting the blood pressure measurement after the uterine contraction is completed.

11. The apparatus set forth in claim 9 and including means for determining whether uterine pressure is rising, falling or stable indicating whether a uterine contraction is occurring, means for periodically initiating maternal blood pressure measurements, means for delaying the blood pressure measurements scheduled during a uterine contraction, and means to initiate a blood pressure measurement after the uterine contraction is completed.

12. A blood pressure measuring apparatus including means for measuring maternal blood pressure, a uterine activity sensor, a processor coupled to said pressure measuring means and the uterine contraction sensor, said processor being programmed to periodically initiate a maternal blood pressure measurement, to sense the occurrence of uterine contractions and to prevent the initiation or continuation of a blood pressure measurement during a uterine contraction and to initiate a blood pressure measurement upon the cessation of the uterine contraction.

13. The apparatus set forth in claim 12 wherein said processor is further programmed to determine whether uterine pressure is increasing, decreasing or stable to identify a uterine contraction, to initiate blood pressure measurements periodically, to determine if a blood pressure measurement is in progress, to terminate any blood pressure measurements in progress if a uterine contraction is occurring and to restart the blood pressure measurement after a time delay.

14. The apparatus set forth in claim 13 wherein said processor is further programmed to average uterine activity samples for a preselected period, to determine the difference between successive uterine activity averages, to determine if the difference is above a positive threshold or below a negative threshold, to determine whether the uterine pressure is rising, falling or stable.

15. The apparatus set forth in claim 14 wherein said processor is further programmed to record rising, falling or stable trends in uterine activity data over multiple periods and to assess the trend to determine whether a uterine contraction is in progress.

16. The apparatus set forth in claim 13 wherein said processor is further programmed to average uterine activity samples for preselected period, to determine the difference between successive uterine activity averages to determine if the difference is above a positive threshold or below a negative threshold, to determine whether the uterine pressure is rising, falling or stable, to prevent the initiation of a blood pressure measurement if uterine blood pressure has established a rising or falling trend characteristic of a uterine contraction, and to initiate a pressure measurement when uterine pressure is stable.

17. The apparatus set forth in claim 9 wherein said processor is further programmed to record trends in uterine activity data over multiple periods and to assess the trend to determine whether a uterine contraction is in progress.

* * * * *